(12) United States Patent
Leitner et al.

(10) Patent No.: US 7,492,930 B2
(45) Date of Patent: Feb. 17, 2009

(54) METHOD AND APPARATUS FOR CAPTURING INFORMATION ASSOCIATED WITH A SURGICAL PROCEDURE PERFORMED USING A LOCALIZATION DEVICE

(75) Inventors: François Leitner, Uriage (FR); Christoph Georg Reuter, Wurmlingen (DE)

(73) Assignee: Aesculap AG (DE)

( * ) Notice: Subject to any disclaimer, the term of this patent is extended or adjusted under 35 U.S.C. 154(b) by 791 days.

(21) Appl. No.: 10/357,908

(22) Filed: Feb. 4, 2003

(65) Prior Publication Data

US 2004/0151354 A1 Aug. 5, 2004

(51) Int. Cl.
G06K 9/00 (2006.01)

(52) U.S. Cl. ...................................... 382/128

(58) Field of Classification Search ................. 382/103, 382/128
See application file for complete search history.

(56) References Cited

U.S. PATENT DOCUMENTS

| | | | | |
|---|---|---|---|---|
| 2,990,765 A * | 7/1961 | Winzenburg | ................. | 396/14 |
| 4,963,903 A * | 10/1990 | Cane | ......................... | 396/428 |
| 5,299,288 A | 3/1994 | Glassman et al. | | |
| 5,769,861 A | 6/1998 | Vilsmeier | | |
| 5,873,822 A | 2/1999 | Ferre et al. | | |
| 6,122,541 A * | 9/2000 | Cosman et al. | ............. | 600/426 |
| 6,184,922 B1 | 2/2001 | Hagihara et al. | | |
| 6,514,259 B2 | 2/2003 | Picard et al. | | |
| 6,827,723 B2 * | 12/2004 | Carson | ....................... | 606/130 |
| 6,877,239 B2 | 4/2005 | Leitner et al. | | |
| 6,920,347 B2 | 7/2005 | Simon et al. | | |
| 2002/0087171 A1 | 7/2002 | Kanesaka | | |
| 2002/0183610 A1 | 12/2002 | Foley et al. | | |
| 2002/0188194 A1 | 12/2002 | Cosman | | |
| 2004/0030245 A1 | 2/2004 | Noble et al. | | |
| 2004/0106926 A1 | 6/2004 | Leitner et al. | | |

FOREIGN PATENT DOCUMENTS

| | | |
|---|---|---|
| DE | 196 39 615 | 4/1998 |
| DE | 101 05 822 | 8/2002 |
| DE | 203 04 153 | 5/2003 |
| EP | 1 033 113 | 9/2000 |
| FR | 2 828 801 | 2/2003 |
| JP | 362047513 A * | 3/1987 |
| WO | WO99/38449 | 8/1999 |

* cited by examiner

Primary Examiner—Tom Y Lu
(74) Attorney, Agent, or Firm—RatnerPrestia

(57) ABSTRACT

A method and apparatus for capturing information associated with a surgical procedure performed using a localization device. The localization device includes sensors that define a field of view in which a marker associated with a surgical tool is tracked. The localization device also includes a camera having a field of view that includes at least a portion of the field of view defined by the sensors. In response to the identification of a designated event (e.g., a signal generated in response to the actuation of a switch by a surgeon), the localization device captures coordinates associated with the surgical tool and captures an image acquired with the camera. In addition, a display screen and/or an endoscopic image associated with the surgical procedure may be captured in response to the designated event. The captured information provides a record of the surgical procedure for use in post operative analysis.

19 Claims, 3 Drawing Sheets

METHOD AND APPARATUS FOR CAPTURING INFORMATION ASSOCIATED WITH A SURGICAL PROCEDURE PERFORMED USING A LOCALIZATION DEVICE

FIELD OF THE INVENTION

The present invention relates to medical instruments and, more particularly, to a method and apparatus for capturing information associated with a surgical procedure performed using a localization device.

BACKGROUND OF THE INVENTION

Localization devices have been developed to assist surgeons in performing surgical procedures. When utilized in a procedure, markers that are observable by a stereoscopic sensor system are attached to bones. The sensor system is connected to a data processing system that records the positions of the markers in space to establish a coordinate reference system relative to each bone bearing a marker. Additional markers may be mounted on surgical tools used to palpate (touch) specific landmarks on the bones while the system records their location in order to ascertain the position of the landmarks in the coordinate reference systems of the bones. Additional markers also may be mounted on surgical tools used to perform the procedure in order to monitor the position of the surgical tools during the procedure. The localization device is preprogrammed with information regarding the position and orientation of the working portion of the tool relative to the marker. Thus, by tracking the marker mounted on the tool, the localization device is able to track the tool itself. A monitor is used to display information developed from the coordinate reference system, the landmarks, and the monitored positions of the surgical tools for use in guiding a surgeon during the procedure, such as navigating a surgical tool to a particular location in the coordinate reference system.

During a surgical procedure, the position and orientation of a surgical tool being navigated by the localization device may be determined for use later in the procedure and/or for post operative analysis. As noted, the position and orientation of the surgical tool are determined by observing a marker mounted on the surgical tool. The marker can be mounted on the surgical tool in only one predetermined way and the localization device is preprogrammed with data indicating the orientation and position of the surgical tool relative to the marker. By observing the marker, the localization device can determine the position and orientation of the surgical tool. Typically, the coordinates of the observed marker are captured and stored in a memory associated with the localization device in response to a designated event, e.g., the actuation of a switch by the surgeon.

The accuracy of the position and orientation of the surgical tool as determined by the localization device is dependent on several factors. These factors include proper mounting of the marker on the surgical tool, accurate preprogramming of the data indicating orientation and position of the surgical tool relative to the marker, and trueness of the marker and surgical tool. If any of these factors are amiss, the position and orientation of the surgical tool as determined by the localization device will be erroneous.

Accordingly, there is a need for capturing information to verify the orientation and position of a surgical tool being navigated by a localization device. The present invention fulfills this need among others.

SUMMARY OF THE INVENTION

The present invention provides a method and apparatus for verifying the orientation and position of a surgical tool as determined by a localization device. The aforementioned need is satisfied by incorporating a camera into a localization device for capturing images of a surgical tool being navigated by the localization device when coordinates of a marker associated with the surgical tool are captured by the localization device. The captured images may then be used to verify the position and orientation of the surgical tool as determined by the localization device based on the captured coordinates for use during post-operative analysis. In certain embodiments, a display screen displayed on a monitor associated with the localization device and/or endoscopic images acquired with an endoscopic camera may additionally be captured to provide further information related to the procedure.

One aspect of the present invention is a method for capturing information associated with a surgical procedure. The method includes monitoring coordinates of a tool with a localization device having a field of view, the tool located within the field of view, and capturing the coordinates of the tool and a field image of a least a portion of the field of view in response to a designated event.

Another aspect of the invention is an apparatus for capturing localization device information. The apparatus includes sensors for sensing a marker associated with a tool, the sensors defining a first field of view; a camera having a second field of view capable of acquiring a field image, the second field of view including at least a portion of the first field of view; a memory; and a computer coupled to the sensors, the camera, and the memory, the computer configured to identify the occurrence of a designated event, the computer prompting the camera to acquire the field image in response to the occurrence of the designated event, the computer capturing and storing in the memory coordinates of the marker associated with the tool and the acquired field image in response to the occurrence of the designated event.

The steps of the method may be embodied in software in a computer readable medium or may form a system comprising means for performing the method steps.

BRIEF DESCRIPTION OF THE DRAWINGS

In the drawings, the same reference numerals are used to indicate the same elements.

DETAILED DESCRIPTION OF THE INVENTION

Figure 1:
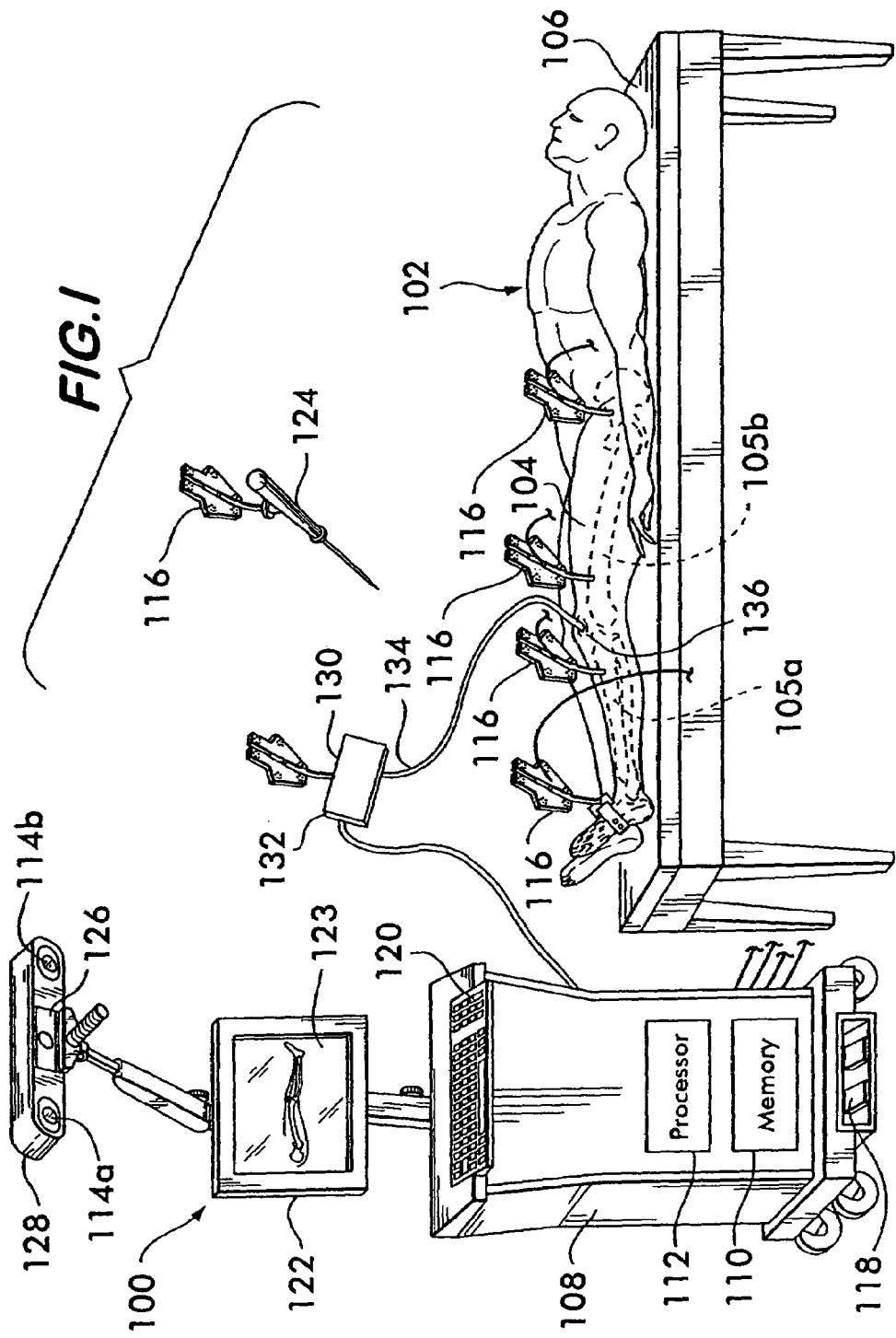
FIG. 1 is an illustration of a patient about to undergo a procedure utilizing a localization device in accordance with the present invention.

FIG. 1 depicts a localization device 100 in which the method of the present invention may be employed. In FIG. 1, a patient 102, who is to undergo a surgical procedure, e.g., a Total Knee Arthroplasty (TKA) procedure on a leg 104, is illustrated schematically lying on an operating table 106. The localization device 100 includes a computer 108 loaded with software for surgical navigation, a memory 110, a processor 112, sensors 114 capable of detecting markers 116, a foot pedal 118, a keyboard 120, and a monitor 122 for displaying a display screen 123 containing surgical navigation information. The display screen 123 is available to a surgeon for guiding the surgeon during surgical procedures performed using the localization device 100. The sensors 114 are mounted on a boom 128 positioned above and laterally from the patient 102 so that the patient's leg 104 is in the field of view of the sensors 114. In general, the markers 116 are fixedly mounted on bones (e.g., tibia 105a/femur 105b) and surgical tools (e.g., pointer 124), so that the localization device 100 can track the exact location and orientation of the bones and surgical tools to which they are mounted. The sensors 114 sense only the markers attached to the bones and surgical tools, rather than bones and surgical tools themselves. Accordingly, the position and orientation of the bones and surgical tools as determined by the localization device based on observing the markers 116 with the sensors 114 are derived, rather than observed directly. A description of a suitable localization device 100 having these features is found in U.S. Pat. No. 6,385,475 to Cinquin et al., having a common inventor and commonly assigned to the same entity as the present application, incorporated fully herein by reference.

In the present invention, the localization device 100 further includes a camera 126. In the illustrated embodiment, the camera 126 is mounted on the boom 128 to which the sensors 114 are also mounted and is connected to the computer 108 of the localization device 100. The camera 126 is configured to acquire an image in response to a signal from the localization device 100. Preferably, images are acquired by the camera 126 and captured in the memory 110 in response to the identification of a predefined signal by the localization device. In a preferred embodiment, the predefined signal is a signal generated in response to a designated event such as the actuation of a switch, e.g., by depressing a foot pedal 118. The camera 126 may be a conventional digital camera, video camera, or essentially any device capable of capturing an image. The selection of a suitable camera 126 and its configuration for use with the localization device 100 will be readily apparent to one of ordinary skill in the related arts.

In the illustrated embodiment, an endoscopic camera 130 is coupled to the localization device 100 for taking endoscopic images of a surgical procedure. The illustrated endoscopic camera 130 includes a housing 132 and a flexible endoscope 134 coupled to the housing 132. The endoscopic camera 130 is connected to the computer 108 of the localization device 100. The flexible endoscope 134 can be inserted into an incision 136, e.g., within a leg 104, to capture images that are not readily visible external to the incision 136. The endoscopic camera 136 generates images that may be displayed within the display screen 123 on the monitor 122 of the localization device 100 in a known manner. The localization device 100 may capture endoscopic images in the memory 110 in response to the identification of a predefined signal. The selection of a suitable endoscopic camera 130 and its configuration for use with the localization device 100 will be readily apparent to one of ordinary skill in the related arts.

Figure 2:
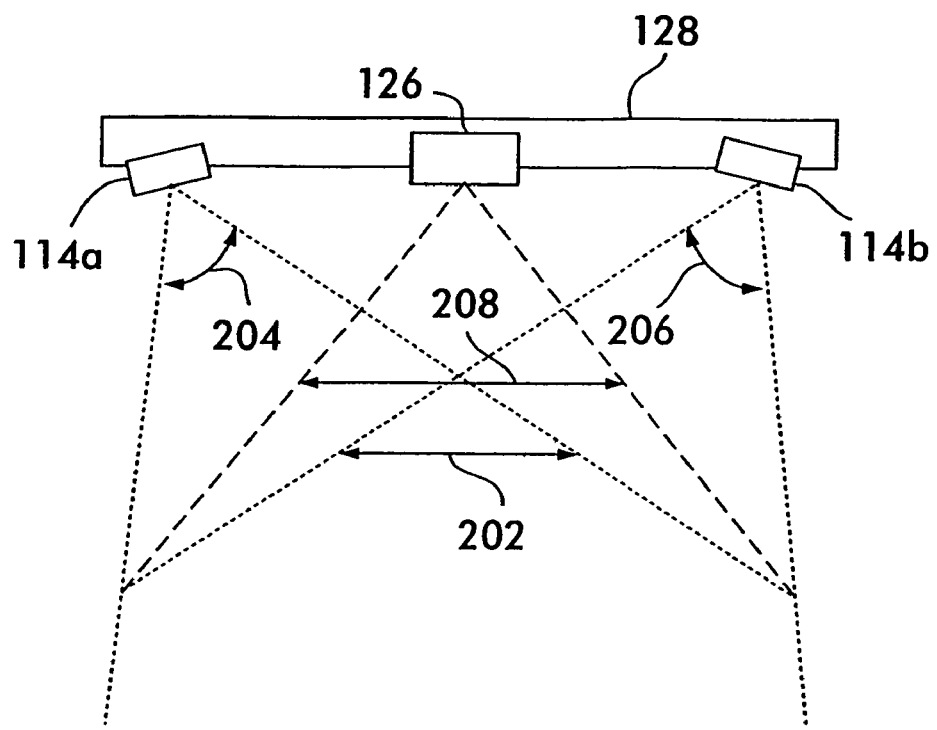
FIG. 2 is an illustration of a first field of view defined by the sensors and a second field of view defined by the camera of the localization device of FIG. 1.

FIG. 2 depicts fields of view associates with the sensors 114 and the camera 126 of the localization device 100 of FIG. 1. The sensors 114 define a first field of view 202. The first field of view 202 represents an area within which the localization device is able to track a marker attached to a surgical tool and, hence, the surgical tool itself. For the illustrated localization device 100, the localization device 100 is capable of tracking a marker as long as the marker is visible by both sensors 114. A first sensor 114a is capable of viewing a first area 204 and a second sensor 114b is capable of viewing a second area 206. The first field of view 202 is the intersection between the first area 204 and the second area 206.

The camera 126 is positioned to capture at least a portion of the first field of view 202 defined by the sensors 114. The camera 126 defines a second field of view 208. The portion of the first field of view 202 capable of being captured by the camera 126 is the area of overlap between the second field of view 208 defined by the camera and the first field of view defined by the sensors 114. Preferably, the area of overlap includes the entire first field of view 202.

It will be recognized by those skilled in the art that additional sensors and/or an omnidirectional sensor may be used to expand the first field of view 202, e.g., to provide up to 360 degrees of coverage surrounding the localization device. Likewise, panoramic cameras and/or multiple cameras may be used to expand the second field of view 208, e.g., up to 360 degrees. In addition, it will be recognized by those skilled in the art that the fields of view 202, 208 may include areas extending to directly above and/or below the localization device 100.

Figure 3:
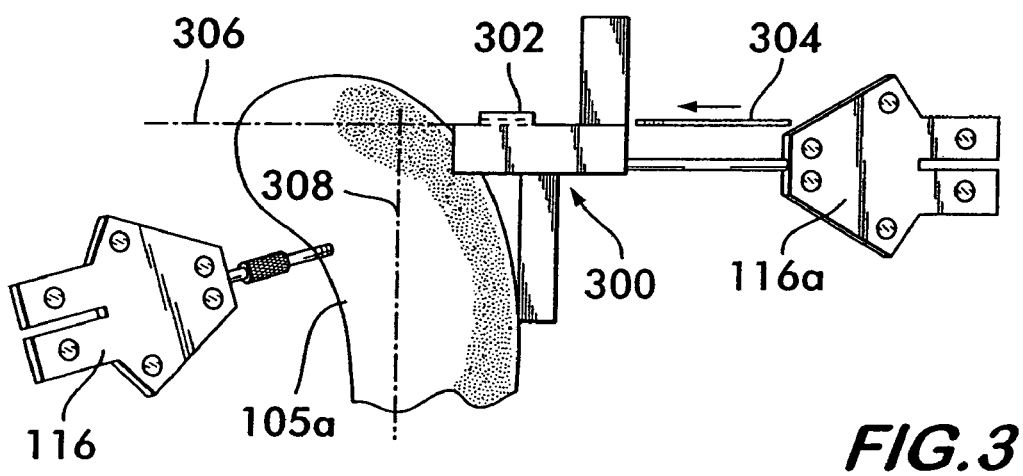
FIG. 3 is an illustration of a cutting jig mounted on a tibia, the cutting jig being navigated by the localization device of FIG. 1.

FIG. 3 depicts a cutting jig 300 positioned on a tibia 105a. The cutting 300 jig is a surgical tool for use during many surgical procedures, e.g., a TKA procedure. For descriptive purposes, an exemplary embodiment of the present invention will be described in connection with the navigation of a cutting jig 300 during a TKA procedure. The TKA procedure involves replacing a damaged knee of the leg 104 (FIG. 1) by resurfacing the tibia 105a and the femur 105b at the knee with metal and/or plastic prostheses to form an artificial joint. The procedure involves sawing off the ends of the tibia 105a and femur 105b near the knee to create surfaces of precise shape and location to accept the prostheses. Although the description of the present invention focuses on capturing information associated with a cutting jig 300 navigated by a localization device 100 during a TKA procedure, it will be readily apparent to those skilled in the art that the present invention may be used with any number of surgical tools in any number of surgical procedures.

The cutting jig 300 is configured to receive a marker 116a for tracking by the localization device 100 (FIG. 1). The localization device 100 is preprogrammed with data that indicates the orientation and position of the cutting slot 302 to the marker 116a mounted on the cutting jig 300. During the procedure, the localization device 100 can observe the marker 116a on the cutting jig 300 and determine the orientation and position of the cutting slot 302 relative to the tibia 105a, which also has a marker 116. During one step of the TKA procedure, the cutting jig 300 is navigated by the localization device 100 and secured to the tibia 105a. The cutting jig 300 is navigated such that, after the cutting jig 300 is secured to the tibia 105a, a cutting slot 302 on the cutting jig 300 is oriented to guide a blade 304 of a saw (not shown) to the proper position for removal of a portion of the tibia 105a. The navigation of a cutting jig 300 by a localization device 100 to perform a cut in a tibia 105a during a TKA procedure is well known to those skilled in the art.

Figure 4:
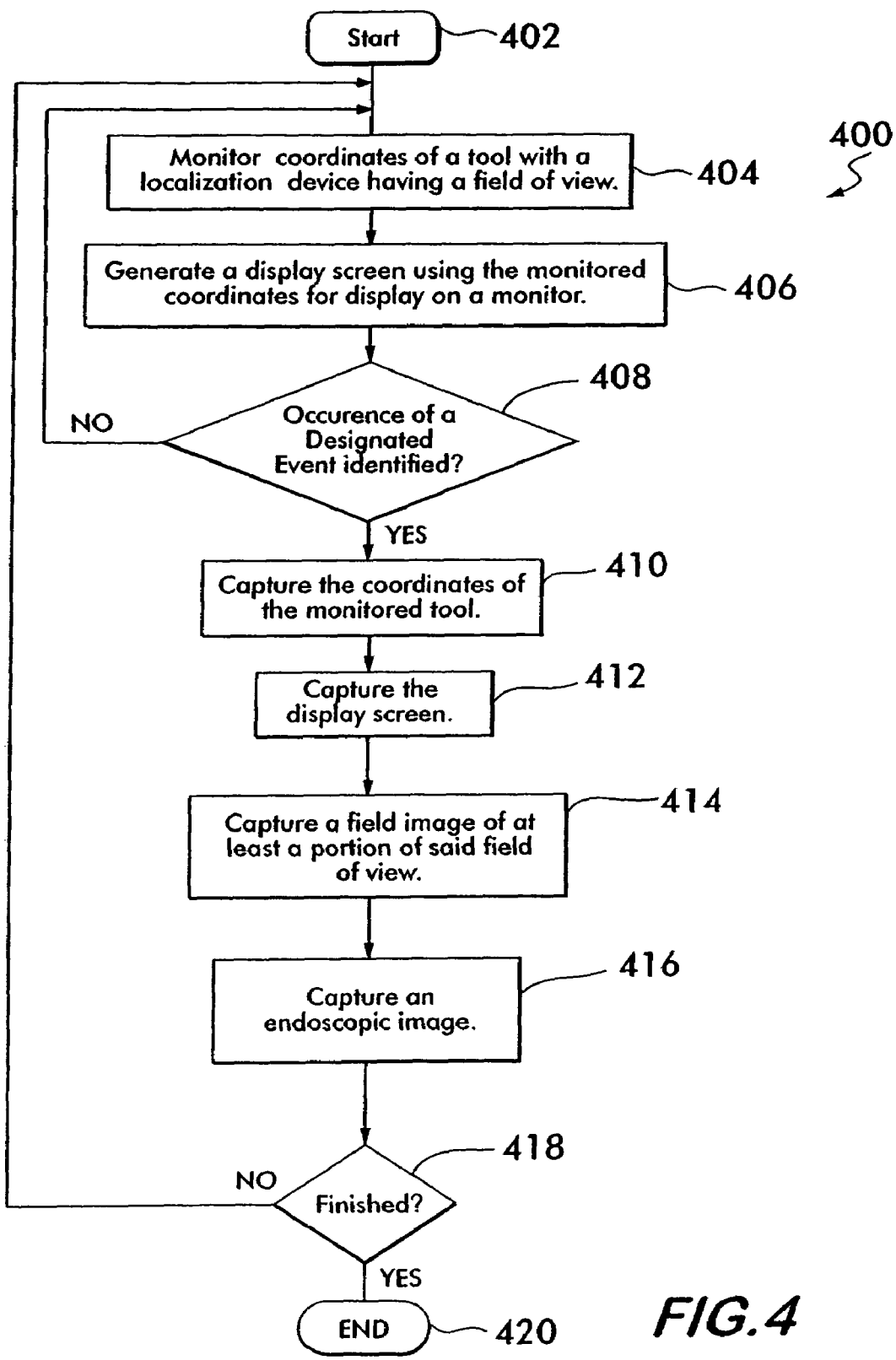
FIG. 4 is a flow chart depicting steps for capturing information associated with a surgical tool navigated by a localization device in accordance with the present invention.

FIG. 4 depicts a flow chart 400 for use in describing a method for capturing images associated with a surgical procedure, e.g., a TKA procedure, in accordance with the present invention. At block 402, the method begins. In a preferred embodiment, the method begins when invoked by the localization device 100 during one or more specific portions of a surgical procedure. For example, the localization device 100 may invoke the method during the navigation of a cutting jig 300 (FIG. 3) for guiding a saw blade 304 to remove a portion of a tibia 105a during a TKA procedure. In an alternative embodiment, the localization device 100 may invoke the method at the start of the surgical procedure and the method may be used to capture visual information throughout the entire procedure.

At block 404, the coordinates of a surgical tool, e.g., a cutting jig, are monitored by the localization device 100. As described above, in reference to FIG. 2, the sensors 114 of the localization device 100 define a first field of view 202 within which a marker may be tracked. By tracking the marker 116, the localization device 100 is able to monitor the coordinates of a surgical tool, e.g., the cutting jig 300, associated with the marker.

At block 406, a display screen 123 is generated for display on the monitor 122 of the localization device 100 of FIG. 1. Preferably, the display screen 123 includes at least some information based on the coordinates of the surgical tool monitored at block 404. For example, the display screen may present a numerical value calculated by the localization device depicting the distance between a leading edge of the cutting slot 302 (FIG. 3) of the cutting jig 300 and a point of interest on the tibia 105. The point of interest on the tibia 105a may be acquired and stored in the memory 110 in a known manner. In certain embodiments, images from the camera 126 and/or endoscopic camera 130 may be included within the display screen 123

At block 408, a check is performed to determine if a designated event has occurred. If the designated event has occurred, processing proceeds at block 410. Otherwise, if the designated event has not occurred, processing proceeds at block 404. In a preferred embodiment, the designated event is the presence of a signal within the computer 108 of the localization device 100. Preferably, the signal is generated in response to the actuation of a switch by a surgeon. The switch may be a key on the keyboard 120, a foot pedal 118, a voice recognition unit, or essentially any device capable of generating a signal in response to an input condition. For example, the localization device 100 may be configured to generate a signal indicative of the designated event when the surgeon depresses the foot pedal 118. In an alternative embodiment, the designated event may be generated automatically by the localization device, e.g., at predefined intervals during a surgical procedure (such as every five minutes).

At blocks 410 and 412, the coordinates of the surgical tool monitored at block 404 and the display screen generated at block 406, respectively, are captured. In a preferred embodiment, the coordinates of the surgical tool and the display screen 123 displayed on a monitor 122 of the localization device at the time the designated event is identified are captured by storing them in a storage medium such as the memory 110 within the localization device 100.

At block 414, a field image of at least a portion of the localization device's field of view is captured. In a preferred embodiment, the field image is an image acquired with the camera 126 connected to the localization device 100 in response to the identification of the occurrence of the designated event. The field image is an image of the surgical procedure being performed using the localization device 100 as "seen" by the localization device. Preferably, the field image includes a visual image of a surgical tool being navigated by the localization device and its surrounding environment. As described above, the sensors 114 define a first field of view 202 within which surgical tools having markers may be tracked. The camera 126 defines a second field of view 208 which includes at least a portion of the first field of view 202. By capturing a field image of the second field of view 208, at least a portion of the first field of view 202 as "seen" by the sensors 114 of the localization device 100 is captured. This information may be useful for post operative analysis, e.g., to verify the coordinates of the cutting slot 302 of a cutting jig 300 with respect to a point on the tibia 105a as determined by the localization device. The field image may include a single image ("snap shot") or a series of images ("movie") captured in response to the identification of the designated event at block 408. In a preferred embodiment, the field image is captured substantially simultaneously with the coordinates of the surgical tool at block 410.

At block 416, an endoscopic image generated by an endoscopic camera, if present, is optionally captured. In a preferred embodiment, the endoscopic image is an image acquired with the endoscopic camera 130 connected to the localization device 100 in response to the identification of the occurrence of the designated event.

At block 418, a determination is made as to whether the specific portion of the procedure in which the method was invoked in block 402 is finished. In a preferred embodiment, the surgeon indicates when that portion of the procedure is finished, e.g., by depressing a foot pedal. If the portion of the procedure is finished, processing proceeds to block 420, where it ends. Otherwise, if the portion of the procedure is not finished, processing proceeds back to block 404 so that the device can continue to capture images in connection with blocks 404 to 416.

Thus, the method can be used to capture images in the following manner. The localization device 100 of FIG. 1 invokes the method of FIG. 4 during a step of a surgical procedure being performed using the localization device 100. During this step of the surgical procedure, the localization device 100 monitors the coordinates of a surgical tool(s) being navigated and generates for display on a monitor 122 a screen display including information associated with the monitored coordinates of the surgical tool. When a switch associated with the localization device 100 is actuated, e.g., by depressing a foot pedal, a signal is generated (i.e., the designated event), thereby prompting the localization device to capture at that instant in time the coordinates of the surgical tool, the display screen, a field image of the surgical procedure, and, optionally, an endoscopic image. The captured information may be integrated into or linked to a conventional report in a well known manner, thus preserving a record of the surgical procedure for post operative analysis.

The captured images provide information about a surgical procedure performed using a localization device 100 (FIG. 1) that can be used to verify the information acquired by the localization device 100 through observation of markers 116 attached to bones and surgical tools. Since the sensors 114 sense only markers mounted on bones and surgical tools, rather than the actual surgical tools on which they are mounted, the position and orientation of a surgical tool as determined by the localization device 100 may not accurately reflect the actual position and orientation of the surgical tool. For example, if the marker is improperly mounted on the surgical tool, the localization device 100 is preprogrammed with incorrect data indicating the orientation and position of the surgical tool relative to the marker, the marker is not true (i.e., is bent), and/or the surgical tool is not true, the position and orientation of the working portion of the surgical tool as determined by the localization device will be erroneous.

Capturing a visual image of the actual surgical tool and its surrounding environment (i.e., a field image) at substantially the same time the coordinates of the marker mounted on a surgical tool as observed by the sensors 114 is captured by the localization device 100 provides a tool for verifying the accuracy of the position and orientation of the surgical tool as determined by the localization device. The captured visual image of the surgical tool may be compared to the position and orientation information for that surgical tool obtained by the localization device to verify the accuracy of that information. For example, assume the surgical tool being navigated by the localization device is a cutting jig 300 (FIG. 3) having a cutting plane 306 defined by a cutting slot 302. Further assume that the cutting slot should be oriented perpendicular to a mechanical axis 308 of the tibia 105a for cutting the tibia. When the cutting jig 300 is navigated by the localization device, the localization device will navigate the cutting jig 300 such that the assumed cutting plane 306 of the cutting jig 300 appears perpendicular to the mechanical axis 308. If the marker is bent, however, the actual position and orientation of the cutting plane 306 as determined by the localization device will be erroneous and the cutting plane 306 will not actually be perpendicular to the mechanical axis 308.

Capturing a visual image of the cutting jig 300 mounted on the tibia 105a allows an analyst to visually examine an image of the cutting jig 300 mounted on the tibia 105a. If upon visual examination, the analyst observes that the cutting plane 306 is perpendicular to the mechanical axis 308 of the tibia 105a, the analyst can verify the accuracy of the position and orientation of the cutting jig as determined by the localization device. On the other hand, if the analyst observes that the cutting plane 306 defined by the cutting slot 302 is not perpendicular to the mechanical axis 308 of the tibia 105a, the analyst can verify the inaccuracy of the position and orientation of the cutting jig as determined by the localization device. Thus, the visual image (i.e., field image) may be used to verify the position and orientation of the cutting jig as determined by the localization device.

Having thus described a few particular embodiments of the invention, various alterations, modifications, and improvements will readily occur to those skilled in the art. Such alterations, modifications and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A method for capturing information associated with a surgical procedure, said method comprising the steps of:
    monitoring coordinates in three dimensions of a tool with a first sensor of a
    localization device having a field of view, said tool located within said field of view; and capturing said coordinates of said tool with said first sensor in response to a designated event; and
    capturing a field image of a least a portion of said field of view including an image of said tool with a second sensor in response to said designated event.

2. The method of claim 1, wherein said coordinates of said tool and said field image are captured substantially simultaneously in response to said designated event.

3. The method of claim 1, further comprising: generating a display screen using one or more of said monitored coordinates; and
    wherein said capturing said field image step comprises capturing an image of data displayed on at least a portion of said display screen in response to said designated event.

4. The method of claim 1, further comprising:
    capturing an endoscopic image associated with the surgical procedure in response to said designated event.

5. The method of claim 1, wherein said designated event is a manual input during the surgical procedure.

6. The method of claim 1, wherein said designated event is a predefined point in time during the surgical procedure.

7. The method of claim 1, wherein said capturing said field image step comprises at least the step of:
    acquiring a single image of said field of view with a camera.

8. The method of claim 1, wherein said capturing said field image step comprises at least the step of:
    acquiring a series of images of said field of view with a video camera.

9. A method for capturing information associated with a surgical procedure, said method comprising the steps of:
    monitoring coordinates in three dimensions of a tool with a first sensor of a localization device having a field of view, said tool located within said field of view;
    generating a display screen using at least one of the monitored coordinates; and
    capturing with said first sensor of said localization device the coordinates of the monitored tool in response to the occurrence of a designated event identified by said localization device;
    capturing an image of data displayed on at least a portion of the display screen in response to the occurrence of said designated event identified by said localization device; and
    capturing a field image of at least a portion of said field of view in response to the occurrence of said designated event identified by said localization device.

10. The method of claim 9, wherein the coordinates of the monitored tool, said portion of the display screen, and said field image are captured substantially simultaneously.

11. The method of claim 9, further comprising:
    capturing with said localization device an endoscopic image associated with the surgical procedure in response to the occurrence of said designated event identified by said localization device.

12. The method of claim 9, wherein said designated event is generated in response to a manual input during the surgical procedure.

13. The method of claim 9, wherein said designated event is generated automatically by the localization device at a predefined point in time during the surgical procedure.

14. The method of claim 9, wherein said capturing an image of data displayed on at least a portion of the display screen step is performed with a camera of said localization device and said capturing a field image step is performed with said camera.

15. A computer program product embodied in a computer readable medium for capturing information associated with a surgical procedure performed using a localization device, said computer program product comprising:
    computer readable program code for generating a display screen using one or more of said monitored coordinates;
    computer readable program code for capturing said coordinates of said tool monitored by said first sensor in response to a designated event:
    computer readable program code for capturing an image of data displayed on at least a portion of said display screen in response to said designated event: and
    computer readable program code for capturing a field image of at least a portion of said field of view with a camera in response to said designated event.

16. The computer program product of claim 15, said computer readable program code embodied in a computer readable medium further comprising:

computer readable program code for capturing an endoscopic image associated with the surgical procedure in response to said designated event.

17. A system for capturing information associated with a surgical procedure performed using a localization device, said system comprising:

means for monitoring coordinates of a tool with a localization device having a field of view, said tool located within said field of view; and means for capturing said coordinates of said tool in response to a designated event; and means for capturing a field image of a least a portion of said field of view including capturing an image of said tool in response to a designated event.

18. The system of claim 17, further comprising: means for generating a display screen using one or more of said monitored coordinates; and wherein said means for capturing a field image captures an image of data displayed on at least a portion of said display screen in response to said designated event.

19. The system of claim 17, further comprising: means for capturing an endoscopic image associated with the surgical procedure in response to said designated event.

* * * * *